(12) United States Patent
Foodman et al.

(10) Patent No.: US 11,756,411 B1
(45) Date of Patent: Sep. 12, 2023

(54) SYSTEM AND METHOD FOR REMOTE INSPECTION OF EQUIPMENT MECHANICAL DIAL GAUGE READINGS, ELECTRICAL TERMINATION AND BUSHING CONDITION MONITORING

(71) Applicant: Aderis Energy, LLC, Cornelius, NC (US)

(72) Inventors: Adam Will Foodman, Charlotte, NC (US); Bradley Allan Micallef, Davidson, NC (US); Olee Joel Olsen, Jr., Cornelius, NC (US)

(73) Assignee: Aderis Energy, LLC, Cornelius, NC (US)

( * ) Notice: Subject to any disclaimer, the term of this patent is extended or adjusted under 35 U.S.C. 154(b) by 220 days.

(21) Appl. No.: 17/216,809

(22) Filed: Mar. 30, 2021

Related U.S. Application Data

(63) Continuation of application No. 16/826,891, filed on Mar. 23, 2020, now abandoned.

(60) Provisional application No. 62/821,654, filed on Mar. 21, 2019.

(51) Int. Cl.
*G08B 29/02* (2006.01)
*G08B 21/18* (2006.01)
*G01N 33/00* (2006.01)
*G01R 31/12* (2020.01)
*G01M 3/04* (2006.01)

(52) U.S. Cl.
CPC ......... *G08B 29/02* (2013.01); *G01N 33/0063* (2013.01); *G01R 31/1245* (2013.01); *G08B 21/18* (2013.01); *G01M 3/04* (2013.01)

(58) Field of Classification Search
USPC ........................................................ 340/506
See application file for complete search history.

(56) References Cited

U.S. PATENT DOCUMENTS

| | | |
|---|---|---|
| 2013/0070099 A1 | 3/2013 | Gellaboina et al. |
| 2013/0147634 A1 | 6/2013 | Abraham, III et al. |
| 2015/0296146 A1 | 10/2015 | Scanlon et al. |
| 2017/0187541 A1 | 6/2017 | Sundaresan et al. |
| 2018/0052008 A1 | 2/2018 | Maman et al. |

OTHER PUBLICATIONS

Information Disclosure Statement (Ids) Letter Regarding Common Patent Application(S), dated May 4, 2022.

*Primary Examiner* — Brent Swarthout
(74) *Attorney, Agent, or Firm* — TILLMAN WRIGHT, PLLC; Chad D. Tillman; James D. Wright

(57) ABSTRACT

An apparatus to locally monitor, and report to a remote monitoring system, specific physical conditions of equipment that provide early indication of failure conditions, including but not limited to: temperature, level of fluids, pressure, temperature, the presence of gases or airborne particulate, and signs leaks.

20 Claims, 3 Drawing Sheets

SYSTEM AND METHOD FOR REMOTE INSPECTION OF EQUIPMENT MECHANICAL DIAL GAUGE READINGS, ELECTRICAL TERMINATION AND BUSHING CONDITION MONITORING

TECHNICAL FIELD AND BACKGROUND OF THE DISCLOSURE

The present disclosure relates broadly and generally to a system and method for remote inspection of equipment mechanical dial gauge readings, electrical termination and bushing condition monitoring.

SUMMARY OF EXEMPLARY EMBODIMENTS

Various exemplary embodiments of the present disclosure are described below. Use of the term "exemplary" means illustrative or by way of example only, and any reference herein to "the invention" is not intended to restrict or limit the invention to exact features or steps of any one or more of the exemplary embodiments disclosed in the present specification. References to "exemplary embodiment," "one embodiment," "an embodiment," "various embodiments," and the like, may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

It is also noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

According to one exemplary embodiment, the present disclosure comprises a system and method for remote inspection of equipment mechanical dial gauge readings, electrical termination and bushing condition monitoring.

Some of the exemplary embodiments and operations of the present disclosure may be computer-implemented as described further herein. Specifically, such implementation may occur in digital electronic circuitry, or in computer software, firmware, or hardware, or in combinations of one or more of them. Embodiments of the present disclosure can be implemented as one or more computer programs, i.e., one or more modules of computer program instructions, encoded on computer storage medium for execution by, or to control the operation of, data processing apparatus. Alternatively or in addition, the program instructions can be encoded on an artificially generated propagated signal, e.g., a machine-generated electrical, optical, or electromagnetic signal, which is generated to encode information for transmission to suitable receiver apparatus for execution by a data processing apparatus. The data processing apparatus may include the sensor, may be part of the sensor, may be a part of a system with the sensor, may be integrated within the system and/or sensor, may be part of receivers, transmitters, components and/or logic associated with the sensor or the receivers and/or transmitters, or any combination thereof. A computer storage medium can be, or be included in, a computer-readable storage device, a computer-readable storage substrate, a random or serial access memory array or device, or a combination of one or more of them. Moreover, while a computer storage medium itself is not a propagated signal, a computer storage medium can be a source or destination of computer program instructions encoded in an artificially generated propagated signal. The computer storage medium can also be, or be included in, one or more separate physical components or media (e.g., other storage devices). Some of the operations applicable in the present disclosure can be implemented as operations performed by a data processing apparatus on data stored on one or more computer-readable storage devices or received from other sources.

Various apparatuses, devices, and machines for processing data, may be used as a "data processing apparatus," including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows applicable in the present disclosure can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Devices suitable for storing computer program instructions and data include all forms of non volatile memory, media and memory devices, including by way of example semiconductor memory devices, e.g., EPROM, EEPROM, and flash memory devices; magnetic disks, e.g., internal hard disks. The processor and the memory can be supplemented by, or incorporated in, special purpose logic circuitry.

To provide for interaction with a user, embodiments of the present disclosure can be implemented on a computer having a display device, e.g., a CRT (cathode ray tube) or LCD (liquid crystal display) monitor, for displaying information to the user and an input device, such as a pointing device, a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

BRIEF DESCRIPTION OF THE DRAWINGS

Exemplary embodiments of the present disclosure will hereinafter be described in conjunction with the following drawing figures, wherein like numerals denote like elements, and wherein.

DESCRIPTION OF EXEMPLARY EMBODIMENTS AND BEST MODE

The present invention is described more fully hereinafter with reference to the accompanying drawings, in which one or more exemplary embodiments of the invention are shown. Like numbers used herein refer to like elements throughout. This invention may, however, be embodied in many different forms and should not be construed as limited to the embodiments set forth herein; rather, these embodiments are provided so that this disclosure will be operative, enabling, and complete. Accordingly, the particular arrangements disclosed are meant to be illustrative only and not limiting as to the scope of the invention, which is to be given the full breadth of the appended claims and any and all equivalents thereof. Moreover, many embodiments, such as adaptations, variations, modifications, and equivalent arrangements, will be implicitly disclosed by the embodiments described herein and fall within the scope of the present invention.

Although specific terms are employed herein, they are used in a generic and descriptive sense only and not for purposes of limitation. Unless otherwise expressly defined herein, such terms are intended to be given their broad ordinary and customary meaning not inconsistent with that applicable in the relevant industry and without restriction to any specific embodiment hereinafter described. As used herein, the article "a" is intended to include one or more items. Where only one item is intended, the term "one", "single", or similar language is used. When used herein to join a list of items, the term "or" denotes at least one of the items, but does not exclude a plurality of items of the list.

For exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

Additionally, any references to advantages, benefits, unexpected results, or operability of the present invention are not intended as an affirmation that the invention has been previously reduced to practice or that any testing has been performed. Likewise, unless stated otherwise, use of verbs in the past tense (present perfect or preterit) is not intended to indicate or imply that the invention has been previously reduced to practice or that any testing has been performed.

Referring now specifically to the drawings, the present disclosure comprises a system and method for remote inspection of equipment mechanical dial gauge readings, electrical termination and bushing condition monitoring.

Figure 1:
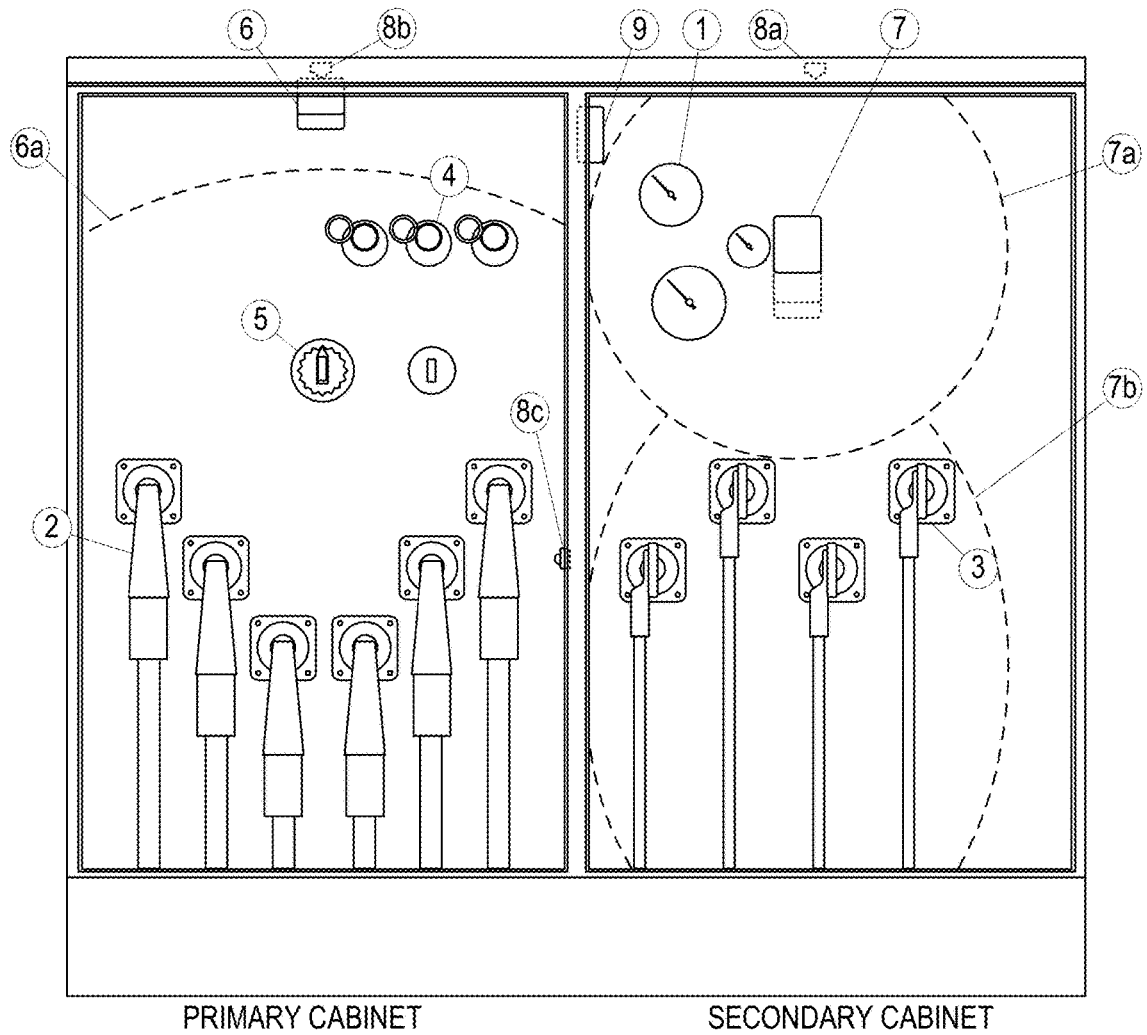
FIG. 1 is a front view of the electrical cabinet incorporating one or more features of the exemplary disclosure.
Figure 2:
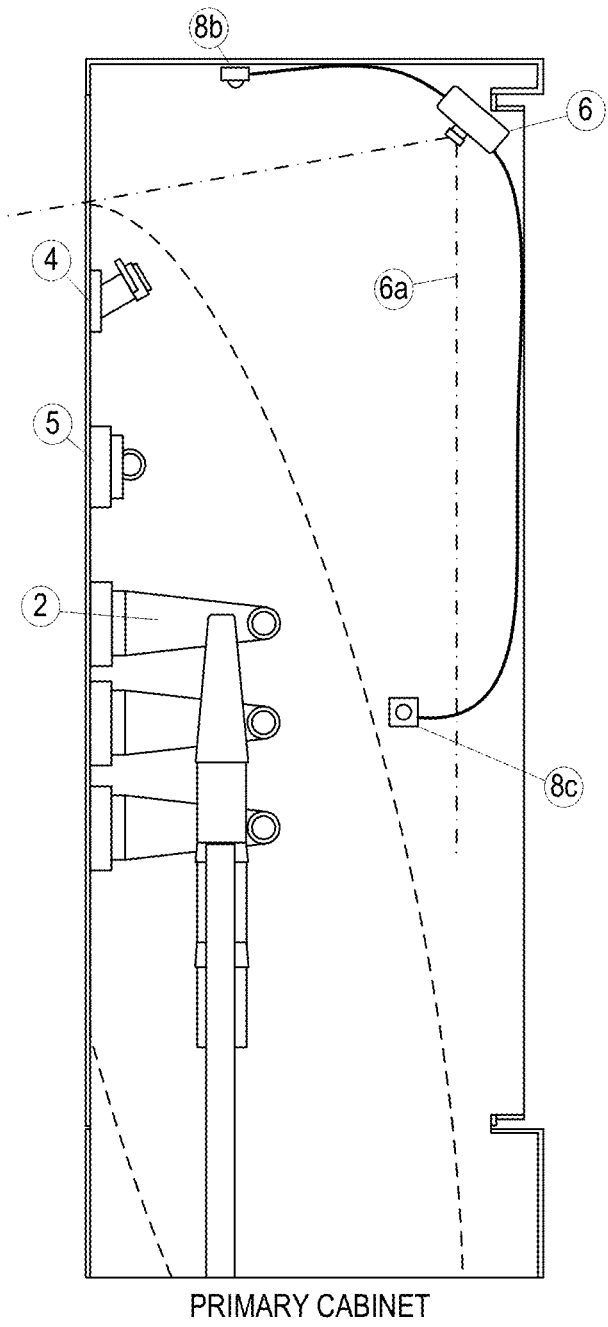
FIG. 2 is a view of the electrical primary section.
Figure 3:
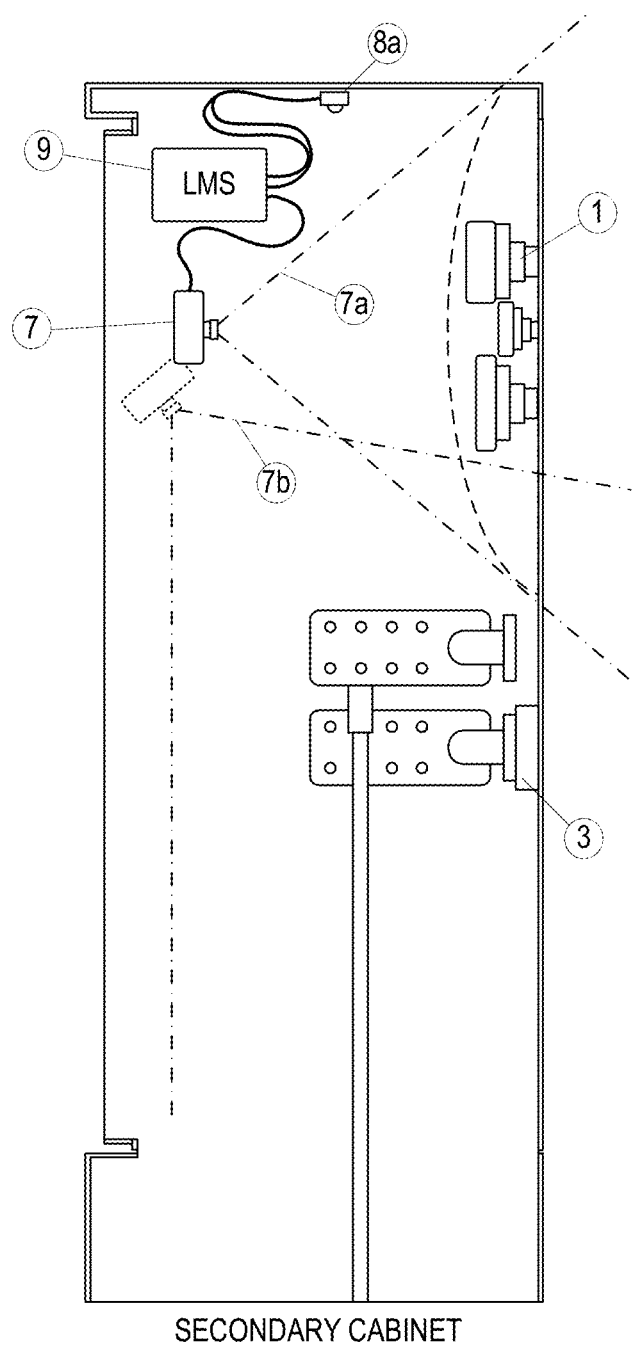
FIG. 3 is a view of the electrical secondary section.

As shown in FIGS. 1, 2, and 3, certain equipment may contain mechanical dial gauges 1 that measure the temperature, level, and cabinet pressure/vacuum through scales that are observed visually by maintenance technician's during manual inspections of the equipment's secondary and primary cabinets. During these inspections, technicians also inspect for any signs of fault conditions, including: (a) electrical discharge 2, (b) signs of thermal damage 3, (c) any evidence of leaking 4 and 5. Inspection of these cabinets may be dangerous due to voltage sources that may remain energized, and isolation of this electrical source is either impractical due to the disruption of associated equipment or processes.

The exemplary apparatus utilizes two high resolution cameras 6 and 7 capable of capturing wide angle images in the low visible-light conditions of the equipment's primary and secondary service cabinets. The primary cabinet's camera is positioned to image 6a the relevant parts of the equipment contained inside the deadfront wall and floor of the cabinet. The secondary cabinet's camera is mounted on a motorized swivel that positions the camera for two separate images: (a) a picture of the mechanical dial gauges 7a, and (b) the other relevant equipment contained in the cabinet 7b, including the deadfront wall and floor of the cabinet. On the roof above both the primary and secondary cabinets two separate gas detectors 8a and 8b are mounted; capable of detecting the presence of airborne particulates. In the lower portion of the primary cabinet, a separate gas detector 8c is mounted, capable of detecting the ozone resulting from electrical arcing events inside the cabinet. The two cameras, and all three gas detectors are connected to a Local Monitoring System (LMS) 9 that receives, stores, and analyzes the inputs from each sensor for the purpose of raising alarms and providing a remote indication potential failure conditions to a remote monitoring system.

The primary and secondary camera images of the deadfront, bushing and floor images will compare a baseline image to determine if leaking in the form of vertical traces, expanding pools, or darkening concrete floor, in a manner that when potential leaks are detected an alarm will be raised. The secondary camera's image of the mechanical dial gauges will use a combination of user defined information about each gauge and an image processing algorithm to determine the value of each gauge and store that value with the time of the image capture, in a manner that changes for each gauge's value can be tracked over time. The three gas sensors will be monitored by the LMS for predetermined levels that define alarming thresholds, in a manner that when a threshold is crossed an alarm will be raised.

The LMS is responsible for coordinating the collection, storage, analysis, and alarming logic for all camera and sensor data. The LMS will be powered from a remote power sources that may vary from installation environments but will primarily use power over ethernet (PoE) for both power and data connection to a remote monitoring system. The LMS will expose data to a remote monitoring system through variety of means based on which remote monitoring system is connected but will primarily use Modbus TCP communication for exposing values and alarm conditions, email for sending alarm details, FTP for transferring image files, and a self-hosted HTTP web browser for allowing user configuration and real-time monitoring and control of the LMS and connected sensors.

For the purposes of describing and defining the present invention it is noted that the use of relative terms, such as "substantially", "generally", "approximately", and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

Exemplary embodiments of the present invention are described above. No element, act, or instruction used in this description should be construed as important, necessary, critical, or essential to the invention unless explicitly described as such. Although only a few of the exemplary embodiments have been described in detail herein, those skilled in the art will readily appreciate that many modifications are possible in these exemplary embodiments without materially departing from the novel teachings and advantages of this invention. Accordingly, all such modifications are intended to be included within the scope of this invention as defined in the appended claims.

In the claims, any means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. Unless the exact language "means for" (performing a particular function or step) is recited in the claims, a construction under 35 U.S.C. § 112(f) [or 6th paragraph/pre-AIA] is not intended. Additionally, it is not intended that the scope of patent protection afforded the present invention be defined by reading into any claim a limitation found herein that does not explicitly appear in the claim itself.

What is claimed:

1. A system for remote inspection and monitoring of equipment mechanical dial gauge readings, electrical termination and bushing condition, said system comprising:
   a plurality of digital cameras capable of capturing wide angle images in low visible-light conditions of an equipment service cabinet;
   a plurality of gas detectors mounted above the equipment service cabinet, and each capable of detecting a presence of airborne particulates; and
   a local monitoring computer system operatively connected to said cameras and said gas detectors and adapted for receiving, storing, and analyzing data inputs for purposes of raising alarms and providing a remote indication of potential failure conditions to a remote monitoring system.

2. An electrical equipment service cabinet equipped with a monitoring system for remote inspection and monitoring, comprising:
   an electrical equipment service cabinet having a roof, a floor, and a deadfront wall supporting one or more mechanical dial gauges, electrical terminations and bushings;
   a digital camera, mounted within the electrical equipment service cabinet, that is capable of capturing wide angle images of the deadfront wall, the floor, or both, in low visible-light conditions of the electrical equipment service cabinet, wherein such images include images of the one or more mechanical dial gauges, electrical terminations and bushings;
   a gas detector, mounted at a top of the electrical equipment service cabinet, that is capable of detecting a presence of airborne particulates; and
   a monitoring computer system operatively connected to the camera and the gas detector and adapted for receiving, storing, and analyzing data inputs from the camera and the gas detector for purposes of raising alarms and providing an indication of potential failure conditions.

3. The monitoring system-equipped cabinet of claim 2, wherein the digital camera is mounted on a motorized swivel.

4. The monitoring system-equipped cabinet of claim 3, wherein the motorized swivel positions the digital camera to capture separate images at a plurality of different orientations.

5. The monitoring system-equipped cabinet of claim 4, wherein the motorized swivel positions the digital camera to capture, at a first orientation, an image of at least one of the one or more mechanical dial gauges supported on the deadfront wall, and, at a second orientation, a separate image of other relevant equipment contained in the cabinet, including equipment on the floor of the cabinet, such equipment including at least one electrical termination or bushing.

6. The monitoring system-equipped cabinet of claim 2, wherein the cabinet includes a primary cabinet and a secondary cabinet, the primary cabinet and secondary cabinet being separated by a partition, wherein the digital camera is a first digital camera that is mounted in the primary cabinet, and wherein the monitoring system-equipped cabinet includes a second digital camera mounted in the secondary cabinet.

7. The monitoring system-equipped cabinet of claim 2, wherein the digital camera images relevant parts of equipment on the deadfront wall, floor, or both.

8. The monitoring system-equipped cabinet of claim 7, wherein the images are adapted for identifying leaking in the form at least one of vertical traces, expanding pools, and darkening concrete floor.

9. The monitoring system-equipped cabinet of claim 2, wherein the digital camera images the one or more mechanical dial gauges.

10. The monitoring system-equipped cabinet of claim 2, wherein the cabinet includes a primary cabinet and a secondary cabinet, the primary cabinet and secondary cabinet being separated by a partition, wherein the gas detector is a first gas detector, mounted at a top of the primary cabinet, and wherein the monitoring system-equipped cabinet includes a second gas detector mounted at a top of the secondary cabinet.

11. The monitoring system-equipped cabinet of claim 2, wherein the monitoring computer system compares images from the digital camera to baseline images.

12. The monitoring system-equipped cabinet of claim 2, wherein the gas detector is a first gas detector, wherein the monitoring system-equipped cabinet includes a second gas detector mounted in a lower portion of the cabinet, and wherein the second gas detector detects ozone resulting from electrical arcing events inside the cabinet.

13. The monitoring system-equipped cabinet of claim 12, wherein the cabinet includes a primary cabinet and a secondary cabinet, the primary cabinet and secondary cabinet being separated by a partition, and wherein the gas detector is disposed in the primary cabinet.

14. The monitoring system-equipped cabinet of claim 13, wherein the gas detector is disposed adjacent the one or more bushings.

15. The monitoring system-equipped cabinet of claim 13, wherein the gas detector is disposed on the partition.

16. The monitoring system-equipped cabinet of claim 2, wherein the one or more mechanical dial gauges include a temperature gauge.

17. The monitoring system-equipped cabinet of claim 2, wherein the one or more mechanical dial gauges include a cabinet pressure/vacuum gauge.

18. The monitoring system-equipped cabinet of claim 2, wherein the monitoring computer system is a local monitoring computer system disposed within the electrical equipment service cabinet.

19. The monitoring system-equipped cabinet of claim 2, wherein the digital camera is capable of capturing wide angle images.

20. A system for remote inspection and monitoring of an electrical equipment service cabinet having a roof, a floor, and a deadfront wall, comprising:
    a digital camera, mounted within the electrical equipment service cabinet, that is capable of capturing wide angle images of the deadfront wall, the floor, or both, in low visible-light conditions of the electrical equipment service cabinet;
    a gas detector, mounted at a top of the electrical equipment service cabinet, that is capable of detecting a presence of airborne particulates; and
    a local monitoring computer system disposed within the electrical equipment service cabinet, operatively connected to the camera and the gas detector, and adapted for receiving, storing, and analyzing data inputs from the camera and the gas detector for purposes of raising alarms and providing a remote indication of potential failure conditions to a remote monitoring system.

* * * * *